United States Patent [19]

Lau et al.

[11] Patent Number: 5,149,764
[45] Date of Patent: Sep. 22, 1992

[54] SUBSTITUTED SILYL-TERMINATED COMPOUNDS AND POLYMERS THEREOF

[75] Inventors: Kreisler S. Y. Lau, Alhambra; Abraham L. Landis, Northridge; Thomas K. Dougherty, Playa del Rey, all of Calif.

[73] Assignee: United States of America as represented by the Secretary of the Navy, Washington, D.C.

[21] Appl. No.: 507,070

[22] Filed: Apr. 10, 1990

Related U.S. Application Data

[62] Division of Ser. No. 73,025, Jul. 14, 1987, Pat. No. 4,935,479.

[51] Int. Cl.$^5$ .............................................. C08G 77/08
[52] U.S. Cl. ............................................ 528/14; 528/27; 528/40; 548/110; 548/217; 548/219
[58] Field of Search ................... 528/10, 14, 27, 40; 548/110, 217, 219

[56] References Cited

U.S. PATENT DOCUMENTS

| | | | |
|---|---|---|---|
| 2,561,429 | 7/1951 | Sueda | 536/431 |
| 3,567,698 | 3/1971 | Kovacs | 528/40 |
| 3,763,204 | 10/1973 | Patterson et al. | 556/432 |
| 4,120,863 | 10/1978 | Tamborski et al. | 548/219 |
| 4,649,207 | 3/1987 | Lau et al. | 549/563 |

FOREIGN PATENT DOCUMENTS

WO86/01511  3/1986  PCT Int'l Appl.
2189788  4/1987  United Kingdom.

*Primary Examiner*—Melvyn I. Marquis
*Assistant Examiner*—R. Dean, Jr.
*Attorney, Agent, or Firm*—Thomas E. McDonnell; Barry A. Edelberg

[57] ABSTRACT

Polymer-ceramic networks in which the polymer chain is anchored in a ceramic network are formed from compounds of the formula

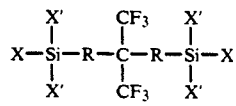

where
X is R', OR', OH, H, Cl, or Br,
X is R', OR', Cl, or Br,
R' is an alkyl group having 1 to 8 carbon atoms, and
R is selected from the group consisting of phenyl and a phenyl-substituted benzoxazole group, or oligomers thereof. Methods of forming the monomer, oligomer, and polymer are disclosed. Related phthalocyanine polymers are also disclosed.

8 Claims, No Drawings

SUBSTITUTED SILYL-TERMINATED COMPOUNDS AND POLYMERS THEREOF

This invention was made with Government support under Contract No. N00014-85-C-0881 awarded by the Department of the Navy. The Government has certain rights in this invention.

This is a division of co-pending application Ser. No. 07/073,025 filed on Jul. 14, 1987, now U.S. Pat. No. 4,935,479.

BACKGROUND OF THE INVENTION

1. Field of the Invention

The present invention relates generally to compounds terminated with substituted silyl groups, to oligomers formed from such compounds, to polymer-ceramic networks formed from such oligomers and compounds, and to processes for forming such compounds, oligomers, and polymers.

2. Description of the Background Art

High-temperature adhesives, coating, and encapsulants are used for a variety of aerospace applications, such as aircraft, missile, and spacecraft structures, where materials must survive temperatures as high as 1000° C. Presently used materials with high temperature capability are generally brittle and very difficult to process, and many degrade in the presence of atmospheric moisture.

One approach to develop high-temperature materials has been to physically blend organic and inorganic materials to produce composite structures which have both the flexibility of organic polymers and the compressive strength of ceramics. The art is replete with the addition of various polymeric resins (most significantly, polymethacrylate type resins) into concrete. The resulting concrete has greatly improved fracture toughness. Alternatively, various inorganic polymers and mixtures of such polymers have been heated at high temperatures to cause the polymers to coalesce into the ceramic fibers. In addition, organic monomers such as the methacrylates have been blended into fluid cement mixtures and then the monomers have been polymerized in situ in concurrrence with the concrete formation process. None of these variations was designed to yield materials which can be used in the 400° to 1000° C. temperature range, as required in many structural and adhesive applications.

The state-of-the-art approach to improve the high temperature performance of organic polymer resins has included the end-capping of a variety of oligomers such as phenylene, imide, ether-ketone-sulfone, phenylquinoxalines, and phenyl-as-triazines with reactive ethynyl end groups. The purpose of using such reactive end groups was to provide a mechanism by which the oligomers could undergo thermally induced chain extension and cross-liking reactions. However, the final cured resins have been found to have less thermo-oxidative stability than the corresponding polymers which did not contain the ethynyl groups, as disclosed by P. M. Hergenrother, *Macromolecules*, Vol. 14, 1981, pages 891 et seq. That the ethynylated oligomers cannot produce cured resins for application above 371° C. was apparently demonstrated by F. E. Arnold and F. L. Hedberg in *Preprints, American Chemical Society Division of Polymer Chemistry*, Volume 21, 1980, pages 176 et seq. The thermo-oxidative instability is ascribed to the presence of non-aromatic end products as a result of the ethynyl groups undergoing thermally induced cross-linking. In fact, solid state carbon-13 NMR studies showed that less than 30 percent of the ethynyl groups had undergone thermal cyclic trimerization to yield stable aromatic rings (M. D. Sefcik, E. O. Stejskal, R. A. McKay, and J. Schaefer, *Macromolecules*, Vol. 12, 1979, pages 423 et seq. U.S. Pat. No. 4,528,216 discloses a process for forming heat resistant resin films by mixing a polyimide resin precursor solution, i.e. a polyamic acid solution, with an organosilicic compound solution which comprises a silicon compound of the formula RnSi(OH)4-n, an additive such as a glass forming agent, and an organic binder in an organic solvent, by depositing the mixture on a silicon substrate and heating up a temperature gradient of 80–500° C. for one hour. Optionally, a minor portion of the silicon compound may be replaced with PO(OH)(OR)2. The product is characterized as having Si—O—Si and polyimide molecular structures and is referred to as a "silicon polyimide resin film." The product formed by the process of U.S. Pat. No. 4,528,216 comprises a mixture of a polyimide component and a Si—O-Si component.

With regard to the ceramic component of prior art polymer-ceramic composites, the feasibility of preparing refractory materials at very low temperatures has produced materials stable well beyond 700° F. (371° C.). For example, aluminum phosphate-based glass material is refractory up to 1600° C., at which point aluminium phosphate begins to decompose. The processing is typically carried out at low temperature and heat treatment requires only temperatures as low as 100° C., as disclosed by Birchall and Kelly, *Sci Amer.*, Vol. 248, No. 5, 1983, pages 104 et seq. The related silicon alkoxide-based materials, made also at low temperatures, have been the subject of intense studies, as disclosed by B. E. Yoldas, *J. Mat. Sci.*, Vol 12, 1977, pages 1203 et seq. and *J. Mat. Sci.*, Vol. 14, 1979, pages 1843 et seq. In principle, these types of glass materials can be reinforced with polymer fibers. The low temperature aspect in processing allows the preparation of polymerceramic composite materials based on many otherwise hard-to-process high temperature polymers.

Modern ceramic processing places strong emphasis on the chemical processes which lead to particles with controllable purity, uniformity in size and submicronic dimensions. These two features will ultimately lead to attainment of maximum theoretical density. There are two fundamental methodologies to address this micromorphology requirement. The solgel process, which has been widely used in making fine powder of various metal oxides, involves the conversion of a sol to gel by means of polymerization. On gradual heating, the gel is converted to fine powder or glass. This method can produce extremely homogeneous mixtures of two or more components, since mixing of these ingredients takes place at the molecular level. An alternative method (referred to as Barringer's procedure) is to generate a colloidal dispersion of the metal oxide, followed by precipitation of essentially uniform submicron particles. As previously mentioned, the superfine nature and uniform size of the powder are conducive to producing ceramic structures with greater than 99% of the theoretical maximum density.

With regard to high-temperature polymers, compounds possessing the hexafluoroisopropylidene group are well known for their thermo-oxidative stability. Their diphenyl derivatives in particular are known for their contribution to the optical transparency of polymers containing them. They are also thermo-oxidatively stable. However, these materials do not have the dimensional integrity and solvent resistance that are desired for many uses. U.S. Pat. No. 4,503,254 assigned to the present assignee, discloses the conversion of 2,2-bis(4-hydroxyphenyl)hexafluoropropane (commercially available as Bisphenol AF) to 2,2-bis(4-halophenyl)hexafluoropropane which can be used to produce a precursor material for subsequent derivatization to produce thermally stable resins for use in high temperature structural composites. Similarly, the art is replete with other substituents besides halogen being substituted on the phenyl group of Bisphenol AF to produce other pertinent intermediates. Some of these other substituents include ethynyl, phenylethynyl, epoxy and amides. These compounds have typically been used as intermediates in forming other resins.

Thus, in view of the previous discussion, it can be seen that a need exists for a polymer which is stable at high temperature, moisture insensitive, tough and easily processible.

SUMMARY OF THE INVENTION

The general purpose of the present invention is to provide a new group of compounds from which oligomers may be derived or formed for subsequent use in forming novel polymer-ceramic networks which are resistant to high temperatures and are easy to process. These compounds and the novel processes for forming them possess most, if not all, of the advantages of the above prior art compounds while overcoming their above-mentioned significant disadvantages.

The above-described general purpose of the present invention is accomplished by providing a new group of compounds terminated with substituted silyl groups. These compounds have formula I below.

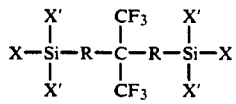

where
X is OR', OH, H, Cl, or Br,
X' is OR', Cl or Br,
R' is an alkyl group having 1 to 8 carbon atoms, and
R is selected from the group consisting of phenylene and benzoxazole group substituted with a phenylene group on the oxazole moiety.

The compounds of formula I are formed by reacting a compound of formula II below

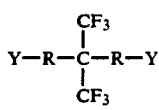

where
R is as defined above,
Y is a halogen
with an alkyl lithium compound in about a 1:2 molar ratio in a solvent to form a reaction mixture, which is then gradually added to an excess of silicon halide having formula III

where
Hal is Cl or Br,
X and X' are as defined above
to form the desired compound or the precursor thereof. For the compound of formula I where X is OR' and X' is OR' or where X is OH and X' is R', the procedure described above is followed to form the corresponding compounds of formula I where X and X' are Cl or Br, or where X is Cl or Br and X' is R'. These latter compounds are then reacted with a compound having the formula

R'OH or

where
R' is as defined above
to convert the Si—halogen bonds to Si—OR or Si—OH. For the remaining compounds of formula I, reaction with R'OH or H₂O is not required.

In accordance with the present invention, compounds of formula I above are the basis for a new group of oligomers of formula IV below.

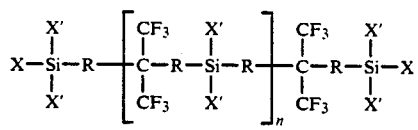

where
R, X, and X' are as defined above and
n is an integer from 1 to about 10.

The compounds of formula IV above are formed by reacting the compound of formula II above with an alkyl lithium compound in a molar ratio of about 1:2 in a chosen solvent to form a reaction mixture. To this reaction mixture there is gradually added a silicon halide having formula III

where
Hal is Cl or Br,
X and X' are as defined above
to form the desired compound or the precursor thereof. For the compound of formula IV where X is OR' and X' is OR' or where X is OH and X' is R', the procedure described above is followed to form the corresponding compounds of formula IV where X and X' are Cl or Br, or where X is Cl or Br and X' and R'. These latter compounds are then reacted with a compound having the formula

R'OH or $$\text{H}_2\text{O}$$

where

R' is as defined above to convert the Si—halogen bonds to Si—OR or Si—OH. For the remaining compounds of formula IV, reaction with R'OH or H₂O is not required.

Alternatively, the oligomers of formula IV above may be formed by hydrolysis or catalysis of the monomer of formula I above.

Further, in accordance with the present invention, the monomers of formula I and the oligomers of formula IV above are used to form a new group of polymer-ceramic networks in which the polymer chain is anchored in a ceramic matrix. This polymer-ceramic network is formed by the solgel polymerization of the monomer of formula I or the oligomer of formula IV above.

Accordingly, it is a purpose of the present invention to provide a polymer which is stable at high temperatures, moisture insensitive, tough, and easily processed.

Another purpose of the present invention is to provide a polymer-ceramic network in which the polymer chain is anchored in a ceramic matrix.

Still another purpose is to provide a process for forming the above-noted polymer-ceramic networks by sol-gel polymerization.

Another purpose of the present invention is to provide oligomers from which the above-noted polymer-ceramic networks may be formed.

Yet another purpose is to provide a process for forming the above-noted oligomers.

A further purpose of the present invention is to provide monomers upon which the above-noted oligomers are based and from which they may be formed.

Another purpose is to provide monomers from which the above-noted polymer-ceramic networks may be formed.

Still another purpose is to provide a process for forming the above-noted monomers.

Another purpose of the present invention is to provide a new method for forming a polymer-ceramic network containing phthalocyanine groups.

The foregoing and other objects, features and advantages of the present invention will be apparent from the following more particular description of the preferred embodiments of the invention.

DETAILED DESCRIPTION OF THE INVENTION

Polymer-ceramic networks formed in accordance with the present invention comprise a polymer chain which is anchored in a ceramic matrix. The organic moiety in this network contributes flexibility, toughness, and processibility as well as moisture insensitivity and high-temperature stability. The inorganic moiety in this network provides dimensional stability through crosslinking. Both moieties contribute optical transparency to the final product. These polymer-ceramic networks are formed from new oligomer compounds or new monomer compounds as described in greater detail below. The oligomer compounds, in turn, are based on new monomer compounds as also described in greater detail below.

The monomer compounds in accordance with the present invention comprise compounds having formula I below.

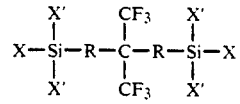
I where

X is OR', OH, H, Cl, or Br,

X' is R', OR', Cl, or Br,

R' is an alkyl group having 1 to 8 carbon atoms, and

R is selected from the group consisting of phenylene and benzoxazole group substituted with a phenylene group on the oxazole moiety.

Preferred compounds of formula I in accordance with the present invention comprise those in which R is phenylene and X and X' are OR', most preferably where R' is methyl or ethyl; or R is phenylene and X and X' are chlorine; or where R is phenylene and each SiXX'₂ comprises (CH₃)₂Si(OH); or where R is phenylene and each SiXX'₂ comprises (CH₃)₂SiH; or where R is benzoxazole substituted with a phenylene group on the oxazole moiety and each SiXX'₂ comprises (CH₃)₂SiOH or (CH₃)₂SiH. In the benzoxazole compounds substituted with a phenylene group on the oxazole moiety of the present invention, C₃F₆ group in formula I is attached to the fused benzene ring of the benzoxazole and the —SiXX'₂ group is attached to the pendant phenylene group on the benzoxazole.

The oligomer compounds in accordance with the present invention comprise compounds having formula IV below.

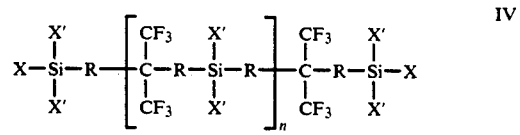
IV where

R, X, and X' are defined above and n is an integer from 1 to about 10.

Preferred compounds of formula IV in accordance with the present invention are those having the same R's, X's and X''s noted above for the preferred compounds of formula I. In the benzoxazole substituted with a phenylene group on the oxazole moiety oligomer compounds of the present invention, the C₃F₆ group in formula IV is attached to the fused benzene ring of the benzoxazole and the —SiXX'₂ or —SiX'₂—group is attached to the pendant phenylene group on the benzoxazole.

The monomer of formula I and the oligomer of formula IV are formed in accordance with the present invention by closely related processes. The monomer of formula I is prepared by reacting a compound of formula II below

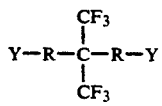
II where

R is as defined above, and

Y is halogen with an alkyl lithium compound in about a 1:2 molar ratio in a solvent to form a reaction mixture. This reaction mixture is then gradually added to an excess of a silicon halide having formula III

where
Hal is Cl or Br,
X and X' are as defined above
to form the desired compound or the precursor thereof. For the compound of formula I where X is OR' and X' is OR' or where X is OH and X' is R', the procedure described above is followed to form the corresponding compounds of formula I where X and X' are Cl or Br, or where X is Cl or Br and X' is R'. These latter compounds are then reacted with a compound having the formula

R'OH or

H$_2$O
where
R' is as defined above
to convert the Si—halogen bonds to Si—OR or Si—OH. For the remainder of the compounds of formula I, reaction with R'OH or H$_2$O is not required.

The oligomer of formula IV is formed by reacting the compound of formula II above with an alkyl lithium compound in a molar ratio of about 1:2 in a chosen solvent to form a first reaction mixture. To this reaction mixture there is gradually added a silicon halide having formula III

where
Hal is Cl or Br,
X and X' are as defined above
to form the desired compound or the precursor thereof. For the compound of formula IV where X is OR' and X' is OR' or where X is OH and X' is R', the procedure described above is followed to form the corresponding compounds of formula IV where X and X' are Cl or Br, or where X is Cl or Br and X' and R'. These latter compounds are then reacted with a compound having the formula
R'OH or H$_2$O
where
R' is as defined above
to convert the Si—halogen bonds to Si—OR or Si—OH. For the remaining compounds of formula IV, reaction with R'OH or H$_2$O is not required. Thus, the order of addition of the silicon halide reactant determines whether the monomer of formula I or the oligomer of formula IV is formed.

The silicon halide reactant used in the present invention has formula III below

where
Hal = Cl or Br
X and X' are as defined above.

Preferred silicon halide reactants comprise silicon tetrachloride, dichlorodimethylsilane, and chlorodimethylsilane. Optionally, the silicon halide reactant may comprise silane substituted with other halogens, such as bromine, and other alkyl groups, such as ethyl.

More specifically, consider the preparation of the monomer and oligomer by the above-described reaction sequence using the reactants 2,2-bis(4-bromophenyl)-hexafluoropropane, an alkyllithium, a silicon tetrahalide, and a lower alcohol. The reactions start by combining the hexafluoropropane compound and an alkyllithium, such as butyllithium, in about a 1:2 molar ratio in suitable solvents such as diethyl ether, tetrahydrofuran, dioxane, or dimethoxyethane. This mixture is then combined with a silicon tetrahalide, most conveniently silicon tetrachloride, which is used in an amount of exact stoichiometry or about one-fold to four-fold excess. If the mixture is added to the silicon tetrachloride (i.e., inverse addition mode commonly employed in organometallic reactions), the resultant product has been found to be predominantly the compound of formula I where X and X' are Cl and R is phenylene. If the silicon tetrachloride is added to the mixture (i.e, normal addition mode), the resultant product has been found to be predominantly the oligomer of formula IV where X and X' are Cl and R is phenylene. Thereafter the lower alcohol, preferably methanol or ethanol, is added to convert the silicon-chlorine bonds to silicon-alkoxy bonds, completing the synthesis of the desired products of formulas I and IV where X and X' are OR and R is phenylene. The butyllithium addition is generally conducted at a temperature of about −78° to −30° C. The silicon tetrachloride and alcohol reactions occur at about ambient temperature, but external cooling may be required in large batch reactions to control the vigor of the reaction. The desired monomer or oligomer is then recovered using a conventional distillation or similar recovery techniques. Alternatively, the oligomers of formula IV may be formed by reacting the monomer of formula I with a reactant which causes the monomer compounds to link together. For the monomer of formula I where R is phenylene and X and X' are OR', hydrolysis with less than a stoichiometric amount of water results in the formation of the corresponding oligomer of formula IV where R is phenylene and X and X' are OR'.

The silanol analogs of the above-noted monomer and oligomer, that is, compounds having formula I and formula IV in which the —SiXX'$_2$ group comprises (CH$_3$)$_2$SiOH, are synthesized from the same dibromo starting material, 2,2-bis(4-bromophenyl)hexafluoropropane, which is converted to the dilithio compound by the action of butyllithium in an appropriate solvent such as tetrahydrofuran, dioxane, or dimethoxyethane. This mixture is treated with dichlorodimethylsilane, which is used in an amount of exact stoichiometry or about one- to four-fold excess. If the mixture is added to dichlorodimethylsilane (i.e., inverse addition), the product is predominantly the compound of formula I where X and X′ are Cl and R is phenylene. If the dichlorodimethylsilane is added to the mixture (i.e. normal mode of addition), the resultant product is predominantly the oligomer of formula IV where X and X′ are Cl and R is phenylene. Thereafter, the products are treated with water and tranformed to the compound of formula I where X and X′ are OH and R is phenyl and the oligomer of formula Iv where X and X′ are OH and R is phenylene. These materials may be used to form polymer-ceramic networks as described herein.

The silyl analogs of the above-noted monomer and oligomer, that is compounds having formula I and formula IV in which the —SiXX′$_2$ group comprises (CH$_3$)$_2$SiH, are synthesized as generally described above, using chlorodimethylsilane as the silicon halide compound and omitting the reaction with R′OH or H$_2$. It should be noted that for this particular compound, diethyl ether cannot be used as an alternative solvent in spite of the fact that it is also commonly used as a solvent for metallation reactions. In diethyl ether, double silylation does not take place and the desired compound is not formed. The compound of formula I where the —SiXX′$_2$ group comprises (CH$_3$)$_2$SiH may be used to form polymer-ceramic networks as described herein, by employing basic conditions. Optionally, the compound of formula I where the —SiXX′$_2$ group comprises (CH$_3$)$_2$SiH can be oxidized under the action of a base such as sodium hydroxide or sodium methoxide, to form the compound of formula I where the —SiXX′$_2$ group comprises (CH$_3$)$_2$SiOH. The latter may be used to form polymer-ceramic networks as described herein. However, it has been found that the compound of formula I having the (CH$_3$)$_2$SiH groups is easier to purify and characterize than the compound of formula I having the (CH$_3$)$_2$SiOH groups.

In accordance with the present invention, the monomer of formula I or the oligomer of formula IV may each be used to form polymer-ceramic networks. First, the monomer or oligomer is dissolved in a selected solvent, preferably one that is miscible with water, such as tetrahydrofuran, ethanol, dioxane, or dimethoxyethane. This step is followed by the addition of water and optionally an inorganic acid catalyst such as hydrochloric acid, sulfuric acid, or phosphoric acid. In such case, the water is used in an amount of about 5 weight percent (wt%) to 10 wt% and the mineral acid is used in an amount of about 0.1% to 0.5%. A new type of cross-linking/networking is established which enhances the high temperature performance of the material. It was, however, noted that the resultant cross-linking/networking reaction produced a product having a relatively low amount of ceramic functionality such that the increase in mechanical ablation resistance and high temperature resistance may not be sufficient for all purposes. To further improve the level of mechanical and thermal resistance of the material, it has been found advantageous to form the polymer-ceramic network by including in the network formation reaction, an alkoxide compound of the formula R″$_m$M(OR′)$_{4-m}$ wherein R′ is an alkyl group having 1 to 8 carbon atoms; R″ is phenyl or an alkyl group having 1 to 8 carbon atoms; M is silicon or a metal which can be selected from the metals listed in the periodic table, among which the most convenient and thus most preferred are aluminum, titanium, or zirconium; and m is an integer from 2 to 4 depending upon the valence of M and the extent of chain extension versus crosslinking that is desired in the final product. Mixed alkoxides such as those containing aluminum and silicon or titanium and silicon, may also be used. It is also advantageous to include R″$_m$M(OR′)$_{4-m}$ and/or (R′O)$_4$Si in proportions such that thermoplasticity due to chain-extension can be tailored. A large proportion of OR′ groups relative to R″ groups results in increased cross-linking, while the reverse results in increased linearity. The use of these metal alkoxide compounds in reactions with polymers allows the incorporation of increased ceramic groups to thereby further increase the mechanical ablation resistance and high temperature resistance of these polymers.

The resultant materials are polymer-ceramic networks, formed by virtue of the synergistic application of polymer and ceramic technologies. The modern ceramic processing technology requires much lower temperature than conventional approaches. The crux of the new technology is in the control of micromorphology, i.e., manufacture of essentially spherical submicron particles of the metal alkoxide which have a high degree of uniformity which serves to increase the ability of orderly packing so that less energy would be required to ultimately coalesce the particles. The superfine uniform-sized particles as a result of hydrolysis-polymerization of metal alkoxides may be prepared through a solgel process which entails the conversion of a sol comprising monomer reactants to a gel by means of polymerization and then gradually heating the gel to densify. Another method is to generate a colloidal dispersion of a metal alkoxide or a mixture of alkoxides followed by precipitation of essentially uniform-sized submicron particles.

While not limiting the present invention to a particular theory of operation, it is believed that the idealized polymer-ceramic network formation reaction would involve first an interaction between the reactive ends of the organic polymer/oligomer with silicon alkoxide by means of a hydrolysis-condensation reaction, and be followed by further polymerization reaction of silicon alkoxide, as indicated below.

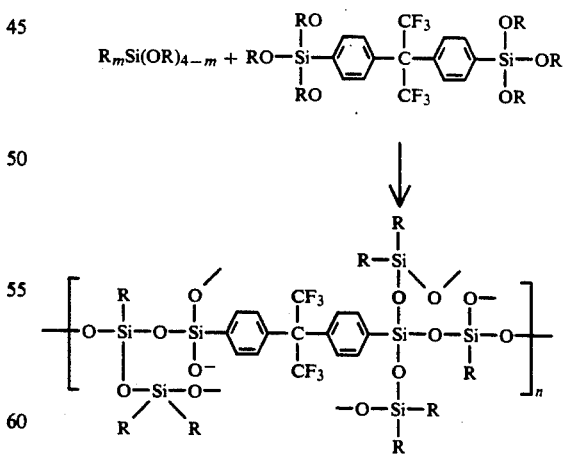

Depending on the nature of the silicon alkoxide compounds, other silylated intermediate oligomers are formed and they also participate in further solgel polymerization by chain extension and branching steps. The attained molecular weight and also the proportion in which these oligomers were present govern the degree of thermoplasticity, toughness and modulus build-up of the ultimate material. It should be noted that the oligomer contains —OR groups along the chain, which groups may also enter into crosslinking/chain extension reactions with each other or with any added metal alkoxides.

Moreover, in accordance with the present invention, we have discovered polymer-ceramic networks of the type described above can also be formed from phthalocyaninesiloxane compounds of formulas V below.

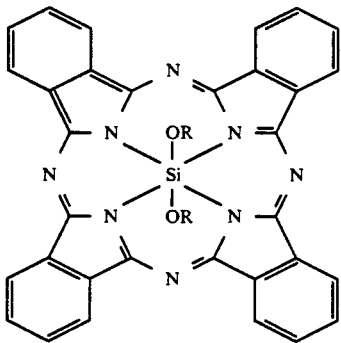

V where
R is

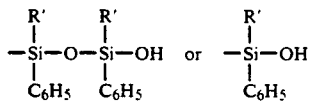

and
R' is an aklyl group having 1 to 4 carbon atoms.
The compounds of formula V are subjected to hydrolysis, such as by reaction with a stoichiometric amount of water, and then dried stepwise over a gradual temperature gradient, followed by a programmed heat treatment to effect curing. The resulting polymers have excellent thermo-oxidative stability.

Examples of practice of the present invention are as follows.

EXAMPLE 1

Preparation of 2,2-Bis(4-bromophenyl) hexafluoropropane.

This example illustrates the preparation of the 2,2-bis(4-bromophenyl)hexafluoropropane reactant in high purity, by a method which was a modification of the process of U.S. Patent No. 4,503,254. This high purity reactant is desirable in order to provide a high yield in the subsequent reactions described herein.

To a slurry of triphenylphosphiine dibromide prepared by dropwise addition of bromine (79.9 g, 1.00 g-atm) to a solution of triphenylphosphine (131 g, 0.500 mole) in 600 ml of dichloromethane, under argon, was added 2,2-bis(4-hydroxyphenyl)hexafluoropropane (84 g, 0.25 mole), which was recrystallized from toluene. The solvent was removed by distillation to leave a solid reaction mixture, and the reaction mixture (contained in a flask) was placed in a molten metal bath at 350° C. for two hours. Copious evolution of hydrogen bromide took place. The reaction mixture was cooled to 100° C. and poured into 600 ml of acetonitrile. The acetonitrile solution was transferred to a liquid-liquid extraction apparatus using hexane as the extracting solvent. The extraction was carried out for a period of at least 24 hours. From the cooled hexane extract was obtained a batch of crystalline needles of unreacted 2,2-bis(4hydroxyphenyl)hexafluoropropane (approximately 14 g). The hexane filtrate was concentrated to a waxy crude product (99 g, 86%) which was purified by distillation at 153–160° C./10$^{-3}$torr. A second distillation at 149–152°. C./5×10$^{-4}$torr gave 85.1g of a crystalline white solid which had a melting point of 79° C.

Alternative to the above procedure, the following procedure was used in a second run. The hexane extract was concentrated to a waxy solid mass. Dichloromethane (500 ml) was added to dissolve the solid and the solution was washed 3 times with 100-ml portions of 20% sodium hydroxide solution and 3 times with 100-ml portions of saturated sodium chloride solution. After drying, the dichloromethane solution was concentrated to yield a crystalline white solid (90 g, 77.9% of theory) which had a melting point of 77° C. Recrystallization from hexane raised the melting point to 79° C. The purity was ascertained by capillary gas chromatographic analysis. The product was characterized as follows:

IR (KBr) 1590(w), 1495(m), 1245(s), 1208(s), 1171(s), 818(m) cm$^{-1}$ NMR (CDCl$_3$) δ7.61, 7.46, 7.30, 7.15 ppm (aromatic, para-substitution pattern).

Analysis for $C_{15}H_8F_6Br_2$:

|       | C     | H    | F     | Br    |
|-------|-------|------|-------|-------|
| Calc. | 38.99 | 1.74 | 24.67 | 34.59 |
| Found | 39.03 | 1.75 | 24.70 | 34.68 |

EXAMPLE 2

Preparation of Bis[4-triethoxysilylphenyl]hexafluoropropane monomer

[Compound of formula I where X and X' are ethoxy and R is phenyl]

A one-liter, three-neck flask, fitted with a dropping funnel, Tru-bore stirrer and nitrogen inlet and exit ports, was charged with 2,2-bis(4-bromophenyl)-hexafluoropropane (25.0 g, 0.05424 mole), prepared as in Example 1, first run, and dry tetrahydrofuran (THF) (300 ml). Then butyllithium (2.4 molar solution in hexane, i.e., 0.1085 mole in 45.2 ml) was added dropwise from the dropping funnel while maintaining the reaction at near ambient temperature. After addition of about two-thirds of the butyllithium, the reaction mixture darkened. The reaction mixture was then transferred to a large addition funnel. and added dropwise to a 2-liter, three-neck flask, fitted with a Tru-bore stirrer, reflux condenser, dropping funnel, nitrogen inlet and outlet ports, and a thermometer, and containing silicon tetrachloride (73.7 g, 0.4336 mole representing a four-fold excess). The addition took 30 minutes. Then, absolute ethanol (125ml) was added dropwise maintaining the temperature at ambient. The solvent was removed on a rotary evaporator and the precipitated lithium chloride was filtered off with the aid of a fritted glass funnel. The residue was distilled using a modified Claisen flask and oil bath at 200° C. -220° C. The product which distilled off at <95° C. and 1 torr (1 mm Hg) was mainly tetraethoxysilane. The high boiling residue was distilled in a Kugelrohr distillation apparatus to yield 2.5 g of a viscous liquid product which was determined by NMR to be the desired product slightly contaminated with higher oligomer.

EXAMPLE 3

Preparation of Oligomers of Formula IV Where X and X' are ethoxy and R is phenylene A two-liter, three-neck flask was fitted with a Trubore stirrer, reflux condenser, thermometer, dropping funnel inlet and nitrogen inlet and outlet ports. The flask was charged with 2,2-bis(4-bromophenyl)hexafluoropropane (46.1 grams, 0.100 mole) prepared as in Example 1, and anhydrous THF (500 ml.) Butyllithium (2.4 molar in hexane, i.e., 0.20 mole in 83.3 ml) was then added dropwise over a 45-minute period. The temperature of the reaction mixture reached the reflux temperature of THF (60° C.). The mixture was stirred at ambient temperature for 1 hour, cooled to 0° C., and silicon tetrachloride (34.0 g, 0.20 mole) was added dropwise. The first few drops changed the color of the reaction mixture to light amber The addition took 15 minutes, and then the reaction mixture was stirred for an additional 1.5 hours at ambient temperature. Next absolute ethanol (40 g, 0.87 moles) was added dropwise. The mixture was then concentrated on a rotary evaporator and the lithium chloride was filtered with the aid of a fritted glass funnel. The residue was distilled using a modified Claisen distillation apparatus in an oil bath at 200-220° C. and a pressure of <1.0 torr (mm Hg). The first distillate was mostly tetraethoxysilane. The residue was then distilled in a Kugelrohr molecular distillation apparatus at 220° C. under reduced pressure (<1.0 torr) The distillate (4.0 g) was a viscous oil. It was determined by NMR spectrometry to be consistent with the desired oligomer with an average degree of polymerization of about 2.

EXAMPLE 4

Polymer-Ceramic Network Formation

To prepare a polymer-ceramic network with the compounds of the present invention and to evaluate their performance characteristics, the following solutions were prepared A=1.0 g product of Example 2 in 10 ml anhydrous tetrahydrofuran; B=1.0 g tetramethoxysilane in 10 ml anhydrous tetrahydrofuran; and C=0.24 g water in 10 ml anhydrous tetrahydrofuran. These solutions were then used to prepare networks based on the stoichiometry that one mole of water will hydrolyze 2 moles of ethoxy groups to effect network formation. The compositions prepared were as follows.

| Composition | Components (ml) | | | wt ratio A/B |
|---|---|---|---|---|
| | A | B | C | |
| 1 | 2.4 | 0.6 | 0.6 | 80/20 |
| 2 | 1.8 | 1.2 | 1.2 | 60/40 |
| 3 | 1.2 | 1.8 | 1.8 | 40/60 |
| 4 | 0.6 | 2.4 | 2.4 | 20/80 |

Each of these four compositions was allowed to form networks by slow evaporation over 48 hours. At this point, polymerization had proceeded to the gel state.

The gel was either spin-coated onto a flat glass surface and dried, or allowed to continue the evaporation process until a hard gel was formed. The hardened gel appeared to be glassy and had a high degree of optical transparency (transmission at 500nm was >92%). The resultant products were then each subjected to a programmed heat treatment of 25-100° C. (1 hour), 100° C. (1 hr), and 300° C.(1hr). The heat treated network specimens were evaluated for thermal resistance by thermogravimetry and for oxidation resistance by isothermal gravimetric analysis. The results indicated an enhancement in both thermal and oxidation resistance in comparison with other polymers containing the hexafluoroisopropylidene group, such as the American Hoechst product Sixef-44.

EXAMPLE 5

The procedure described in Example 4 was repeated with the exception that Component B was methyltri(methoxy)silane. The polymer-ceramic network specimens were prepared and processed in an identical manner as Example 4. The hardened gel appeared to be similarly optically transparent as specimens from Example 4. In comparison to specimens prepared in Example 4, these specimens were qualitatively less brittle.

EXAMPLE 6

Preparation of Compound of Formula I Comprising $(CH_3)_2SiH$ and R is phenylene To anhydrous THF(250 ml) at −78° C. was added n-butyllithium in hexane (140 ml, 0.21 mole). To this was added during 0.5 hour 2,2-bis(4-bromophenyl)hexafluoropropane (20.2 g, 0.044 mole). The reaction was stirred at −78° C. for 0.5h. The pale yellow dianion solution was added via a stainless steel canula to a tetrahydrofuran (THF) solution of chlorodimethylsilane (50 g of electrophile in 200 ml of THF) at −78° C. The addition required 0.5h and the reaction was stirred at Dry Ice temperature for an additional hour. The ice bath was removed and the reaction was stirred overnight. The contents of the reaction were concentrated (to about 100 ml) and the mixture was taken up in ether (300 ml) and washed twice with saturated aqueous sodium chloride solution. The clear ethereal solution was dried over magnesium sulfate and evaporated to give 19.2 g (95% yield) of product which was 85% pure by gas chromatographic analysis. The product which crystallized upon standing was recrystallized from cold hexane. The product was identifed as follows:

mp. 50–51° C.; IR(KBr) 2960(sharp, medium), 2130 (strong, sharp), 1300–1150 (v. broad, strong), 880cm$^{-1}$ (broad, strong);

NMR (CDCl$_3$) δ0.38 (d,12H, CH$_3$Si), 4.30(septet, 2H, SiH) and 7.70 ppm (q,8H, aromatic).

Larger batches of this compound were made according to the same procedure. The crude product was distilled at 118–125° C./0.05 torr and the distillate was recrystallized from cold hexane. The product had a melting point of 50–51° C.

EXAMPLE 7

Preparation of Compound of Formula I Comprising Si(CH$_3$)$_2$OH and where R is benzoxazole substituted with a phenylene group on the oxazole moiety A. Preparation of Compound of Formula II where X and X' are Bromine and R is Phenyl-substituted benzoxazole.

The starting material 2,2-bis(3-amino-4-hydroxyphenyl)hexafluoroporpane was synthesized by the procedure described by K.S.Y. Lau, A.L. Landis, W.J.

Kelleghan, and C.D. Beard, *Journal of Polymer Science, Polymer Chemistry Edition*, volume 20, 1982, page 2381 et seq. This compound was allowed to react with 2 equivalents of 4-bromobenzoic acid in the solvent medium made of phosphorus pentoxide ($P_2O_5$) and methanemed sulfonic acid ($CH_3SO_3H$), referred to herein as PPMA. More specifically, a mixture of 2.10 g (0.12 moles) of 4-bromobenzoic acid, 1.83 g of 2,2-bis(3-amino-4hydroxyphenyl)hexafluoropropane and 25 ml of PPMA solution was heated to 150° C. for 4 hours and then cooled to 25° C. before pouring into 200 ml of cold 5% aqueous sodium hydroxide. The precipitate was filtered, dissolved in a 1:1 hexane-dichloromethane mixture, and the solution was dried over anhydrous sodium sulfate. The solution was evaporated to yield 2.0 g (90%) of the desired product 2,2-bis {5-[2-(4-bromophenyl) benzoxazolyl]}-hexafluoropropane, Compound A below, which is compound of formula II where X and X' are bromine and R is benzoxazole substituted with a phenylene group on the oxazole moiety. Purification was carried out by column chromatography using silica gel. The amorphous solid obtained did not yield a well-defined melting point but was identified by its infrared and nuclear magnetic resonance spectra.

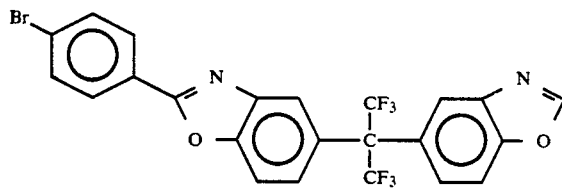

B. Preparation of Compound of Formula I comprising $Si(CH_3)_2OH$ and where R is benzoxazole substituted with a phenylene group on the oxazole moiety.

The general procedure described in Example 2 was followed except that 2,2-bis(4-bromophenyl)hexafluoropropane was replaced with Compound A prepared as described immediately above, and silicon tetrachloride was replaced with chlorodimethylsilane.

EXAMPLE 8

Preparation of Phthalocyanine Compounds

The key compound, 1,3-diiminoisoindole, was synthesized as described by M.K. Lowery, A.J. Starshak, J.H. Espirito, P.C. Krueger and M.E. Kenney, *Inorganic Chemistry*, volume 4, 1965, pages 128 et seq. Batches of 100–200 g scale were routinely prepared in 60–80% yield.

Mp. 192–194° C.

Dichloro(phthalocyanino)silicon was synthesized from 1,3-diiminoisoindole by modification of the preparation procedure described by T.J. Marks et al, *Journal of American Chemical Society*, volume 105, 1983, pages 1539 et seq, as follows. The diiminoisoindole was treated with an excess of silicon tetrachloride in quinoline at 219° C. for two hours. The conversion of diiminoisoindole to dichloro(phthalocyanino)silicon was evident from the formation of an intense blue-purple color. Filtering the reaction mixture at a temperature above 180° C. gave microcrystalline solids, which were analytically pure (by elemental analysis) and in 67% yield. It was important not to allow the reaction mixture to cool below 180° C., to prevent coprecipitation of other extremely fine particles which were undesirable. Infrared spectrum of the blue-purplish crystalline solids matched with the results reported by J.B. Davison and K.J. Wynne, *Macromolecules*, volume 11, 1978, at pages 186 et seq.

Dichloro(phthalocyanino)silicon was converted to dihydroxy(phthalocyanino)silicon (formula V, where R is H) in alkaline aqueous pyridine at 110° for 24 hours. The yield was 95%. The product was characterized by infrared spectroscopy.

The Compound B having formula V where R is

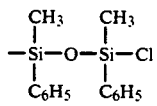

was prepared by reacting the compound of formula V where R is hydrogen with the compound

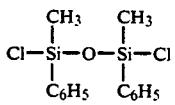

in pyridine and triethylamine at 25° C. for 168 hours.

The reaction product thereof was reacted with water in dioxane and pyridine at 25° C. for 18 hours, to form Compound C having formula V where R is

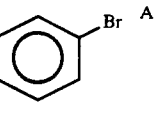

the overall yield from the compound of formula V where R is H to compound C was 36%.

Alternatively, the compound of formula V where R is H was reacted with dichloromethylphenylsilane in pyridine and triethylamine at 70° C. for 40 hours to form Compound D having formula V where R is

The latter compound was then reacted with water in dioxane and pyridine at 25° C. for 18 hours to form Compound E having formula V where R is

The conversion to Compound D was accomplished in 50% yield, but the hydrolysis of Compound D to form Compound E was incomplete. Consequently, the following alternative procedure was used. Compound D was reacted with water is dioxane and pyridine at about 80–100° C. for 72 hours.

For each of the above-described reactions, Fourier-transform NMR spectrometry was used to monitor the reaction course and ascertain product purity.

EXAMPLE 9

Polymer-Ceramic Networks from Phthalocyaninesiloxane Compounds

Compound C and Compound E prepared as described in Example 8 where each formed into polymer-ceramic networks as generally described in Example 4. Compound C or E was described in dioxane and pyridine and was hydrolyzed, for example, by reaction with a stoichiometric amount of water. The resulting materials were cured at 300° for 24 hours. An excellent level of thermo-oxidative stability was demonstrated by iso-thermal gravimetric analysis at 400° C. in air.

Thus, in accordance with the present invention, there are provided polymer-ceramic networks wherein organic polymer technology is combined with low temperature ceramic processing technology to create a synergistic combination of high temperature resistant organic polymers which are chain-extended and cross-linked through ceramic-forming groups to produce networks with improved hardness and thermal resistance as compared to conventional polymers. This enhancement of performance makes these polymer-ceramic networks especially suitable for use as high temperature adhesives, coatings, and the like, in applications where conventional high temperature resistant materials would fail.

What is claimed is:

1. A method of forming a compound of the formula IV

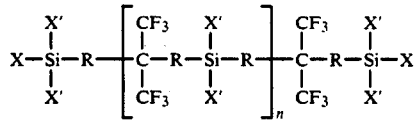

where
R is a benzoxazole group substituted with a phenylene group on the oxazole moiety, the fused benzene ring of the benzoxazole group being attached to the $C_3F_6$ group and the phenylene group on the oxazole moiety being attached to the $-SiXX'_2$ group,
X is H, Cl, or Br,
X' is Cl, or Br, and
n is an integer from 1 to about 10, comprising the steps of:
a) providing a compound of the formula II

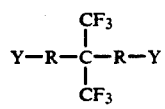

where
Y is a halogen, and
R is as defined above;
b) reacting said compound of formula II with an alkyl lithium compound in a molar ratio of about 1:2 in an appropriate solvent to form a reaction mixture;

c) gradually adding to said reaction mixture a silicon halide having formula III

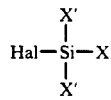

where
Hal is Cl or Br, and
X and X' are as defined above; to form said compound of formula IV.

2. A method according to claim 1 wherein said silicon halide is silicon tetrachloride.

3. A method according to claim 1 wherein said alkyl lithium compound comprises butyl lithium.

4. A method according to claim 1 wherein said solvent is selected from the group consisting of diethylether, tetrahydrofuran, dioxane, and dimethoxyethane.

5. A method of forming a compound of the formula IV

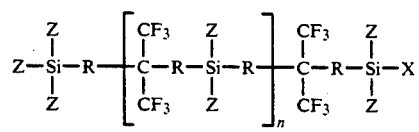

where
R is a benzoxazole group substituted with a phenylene group on the oxazole moiety, the fused benzene ring of the benzoxazole group being attached to the $C_3F_6$ group and the phenylene group on the oxazole moiety being attached to the $-SiXX'_2$ group,
Z is OR',
R' is an alkyl group having 1 to 8 carbon atoms, and
n is an integer from 1 to about 10, comprising the steps of:
a) providing a compound of the formula II

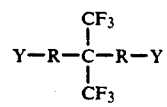

where
Y is a halogen, and
R is as defined above;
b) reacting said compound of formula II with an alkyl lithium compound in a molar ratio of about 1:2 in an appropriate solvent to form a first reaction mixture;
c) gradually adding to said first reaction mixture a silicon halide having formula III

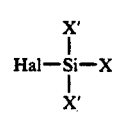

where
Hal is Cl or Br, and
X and X' are Cl or Br;
to form a second reaction mixture;

d) adding to said second reaction mixture a compound of the formula R'OH where R' is an defined above;

to form said compound of formula IV.

6. A method according to claim 5 wherein said compound R'OH is selected from the group consisting of methanol and ethanol.

7. A method of forming a compound of formula IV

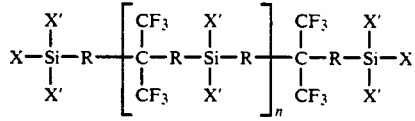

where

R is a benzoxazole group substituted with a phenylene group on the oxazole moiety, such that the fused benzene ring of the benzoxazole group is attached to the $C_3F_6$ group and the phenylene group on the oxazole moiety is attached to the $-SiXX'_2$ group, X is OR', H, Cl, or Br, X' is OR', Cl, or Br, R' is an alkyl group having 1 to 8 carbon atoms, and n is an integer from 1 to about 10, a) providing a compound of formula I

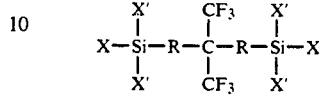

where

R, X, and X' are as defined above; and b) subjecting said compound of formula I to hydrolysis.

8. The method of claim 7 wherein step "b" comprises reaction with a mild acid or base.

* * * * *